United States Patent [19]

Burkinshaw

[11] Patent Number: 5,480,445
[45] Date of Patent: Jan. 2, 1996

[54] INTERLOCKING TIBIAL PROSTHESIS

[75] Inventor: Brian D. Burkinshaw, Pflugerville, Tex.

[73] Assignee: Intermedics Orthopedics, Inc., Austin, Tex.

[21] Appl. No.: 257,680

[22] Filed: Jun. 9, 1994

[51] Int. Cl.[6] ........................................... A61F 2/38
[52] U.S. Cl. ............................................ 623/20; 623/18
[58] Field of Search ................................ 623/20, 18, 16

[56] References Cited

U.S. PATENT DOCUMENTS

| | | | |
|---|---|---|---|
| 4,213,209 | 7/1980 | Insall et al. | 3/1.911 |
| 4,298,992 | 11/1981 | Burstein et al. | 3/1.911 |
| 4,479,271 | 10/1984 | Bolesky et al. | 623/20 |
| 4,743,261 | 5/1988 | Epinette | 623/20 |
| 4,944,757 | 7/1990 | Martinez et al. | 623/20 |
| 4,963,152 | 10/1990 | Hofmann et al. | 623/18 |
| 5,019,103 | 5/1991 | Van Zile et al. | 623/20 |
| 5,062,852 | 11/1991 | Dorr et al. | 623/20 |
| 5,071,438 | 12/1991 | Jones et al. | 623/20 |
| 5,152,797 | 10/1992 | Luckman et al. | 623/20 |
| 5,387,241 | 2/1995 | Hayes | 623/20 |

OTHER PUBLICATIONS

Protek Product Brochure, "Mark II" Knee, 1988.

*Primary Examiner*—David Isabella
*Attorney, Agent, or Firm*—John R. Merkling

[57] ABSTRACT

A tibial knee prosthesis having a plastic or polyethylene prosthesis body comprising an articulating surface and medullary stem. An intermediate metal plate locks on to the medullary stem and fits between the articulating surface and a resected proximal surface of the tibia. A distal surface of the plate may be provided with a porous coating adjacent the proximal resected surface of the tibia, to encourage bone ingrowth and fixation.

16 Claims, 1 Drawing Sheet

INTERLOCKING TIBIAL PROSTHESIS

FIELD OF MY INVENTION

My invention relates to implantable orthopedic prosthesis generally, and specifically to an implantable tibial prosthesis.

BACKGROUND OF MY INVENTION

Implantable orthopedic prostheses to replace human bone joint interfaces are well-known. In particular, it is known to implant a prosthesis on a resected proximal surface of the tibia to articulate with a femoral knee prosthesis. Such prostheses are known, for example, from U.S. Pat. Nos. 4,963,152; 5,062,852; and 5,071,438, assigned to Intermedics Orthopedics, Inc. the assignee of my present invention. Tibial prosthesis frequently comprise a metal baseplate having some form of fixation means to attach the baseplate to the resected surface of the tibia. Such means may include bone screws, pegs, or medullar shafts. Medullar shafts of cruciate shape are also known. On the metal baseplate is attached an articulating surface, frequently made of ultra high molecular weight polyethylene (UHMWPE). In addition, all-polyethylene tibial prostheses have been proposed. Prosthesis with metal baseplates are somewhat complex and expensive to manufacture. On the other hand, all-polyethylene tibial prostheses tend to lack stiffness.

With the foregoing in mind, it has been an object of my invention to provide a tibial prosthesis wherein both the articulating surface and the fixation means were of a common polyethylene part, but which was provided with a metal interface at the proximal end of the tibia.

It has also been an object of my invention to provide such a prosthesis which could be easily assembled. A further object of my invention has been to provide a two-part prostheses which could be easily manufactured.

These and other objects and features of my invention will be apparent from the following description taken with reference to the accompanying drawings.

SUMMARY OF MY INVENTION

My invention comprises a tibial knee prosthesis having a plastic or polyethylene prosthesis body comprising an articulating surface and medullary stem. I have provided an intermediate metal plate, positioned to lock on to the medullary stem and fit between the articulating surface and a resected proximal surface of the tibia. The metal plate stiffens the prosthesis. A distal surface of the plate may be provided with a porous coating adjacent the proximal resected surface of the tibia, to encourage bone ingrowth and fixation. The plate simply slides over the medullary stem and locks in position by rotating around the stem axis.

I will now describe my invention with respect to the accompanying drawings.

DETAILED DESCRIPTION OF MY PREFERRED EMBODIMENT

Figure 1:
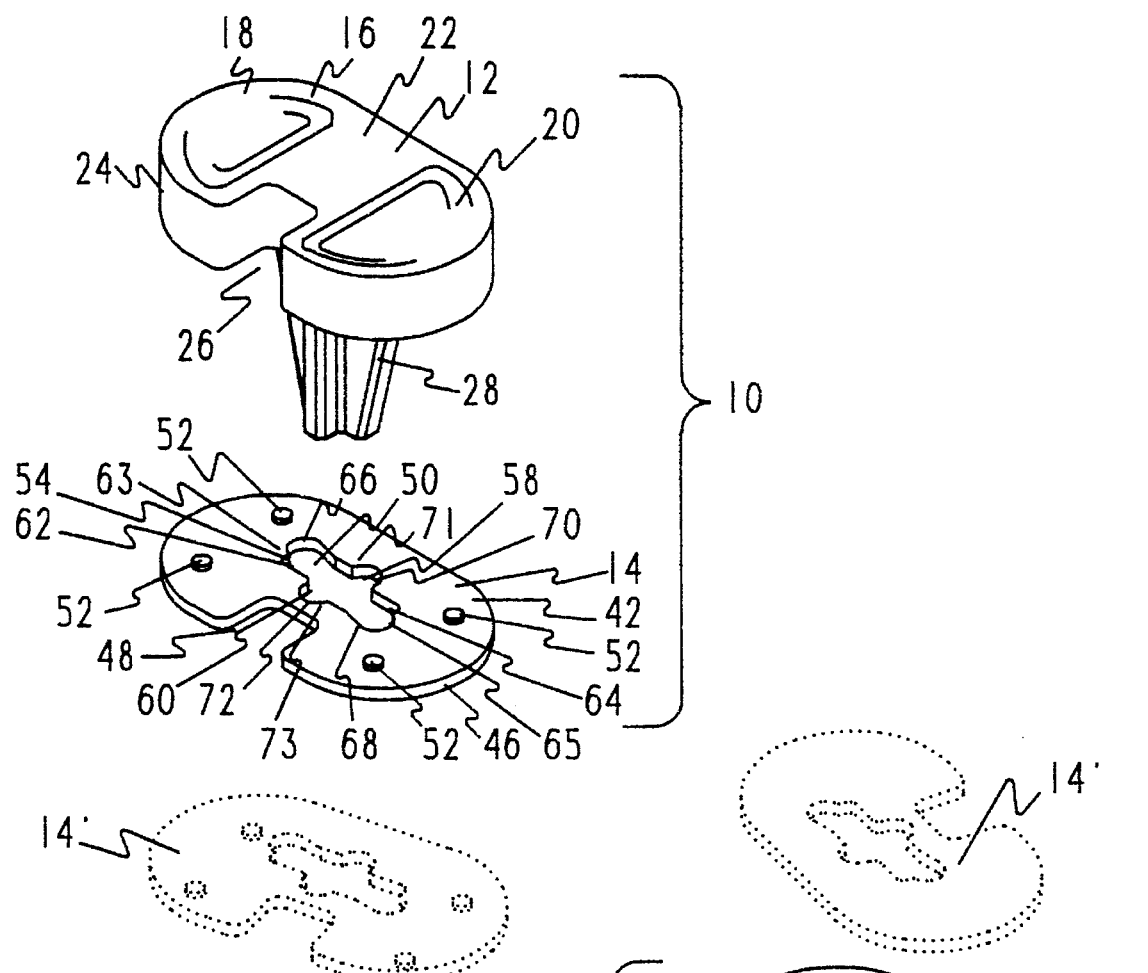
FIG. 1 is an exploded perspective view of a tibial knee prosthesis according to our invention, with a baseplate shown in two positions, in solid and phantom lines.

As illustrated in FIG. 1, my invention comprises a tibial knee prosthesis generally designated 10 consisting of a main body 12 of the prosthesis and an intermediate plate 14. The main body 12 is composed of ultra-high molecular weight polyethylene (UHMWPE) or some other suitable plastic material. An articulating surface 16 has a medial condyle compartment 18 and a lateral condyle compartment 20. An intermediate plateau 22 lies between the condylar compartments 18, 20. As known in the art, the intermediate plateau 22 may be raised with respect to the condyle compartments to provide stability to the knee prosthesis over all. In addition, a substantially raised spine might be provided if a so-called posterior stabilized knee is desired. Examples of posterior stabilized knees may be found in U.S. Pat. Nos. 4,298,992 and 4,213,209. The body 12 further comprises a curved outer edge 24 which is generally ovoid in configuration. In an asymmetric design, the medial side of the prosthesis adjacent the medial condyle compartment 18 has a larger parameter than does the lateral side adjacent the lateral condylar compartment 20. Symmetric designs are more common and may also be used with my invention. The object is to conform generally to the usual anatomical configuration of the human tibia. Posteriorly on the main body 12, a notch 26 can provide clearance for the posterior ligaments of the knee. The notch 26 is not necessary, particularly if a posterior stabilized knee design is desired.

The main body 12 further comprises a medullar stem 28 which extends distally from the articulating part 16. The articulating part 16 and stem 28 are preferably of single-piece molded construction. The stem 28 is cruciate in overall cross-section as can best be seen in FIG. 2. Medial and lateral arms 30, 32 of the stem 28 extend relatively far in medial and lateral directions, respectively, adjacent the body 12 and near a bottom surface 34 thereof. The medial and lateral arms 30, 32 taper distally along the length of the stem. In contrast, anterior and posterior arms 36, 38 do not taper or taper only slightly. This is because of the more restricted area in the anterior posterior direction which is available for the stem. Adjacent the surface 34, each of the arms 30, 32, 36 and 38 has a notch 39 for receiving the intermediate plate 14 as will be described. Also, surface 34 has at least one and preferably a plurality and more preferably four slots or indentations 40 for cooperating with the intermediate plate 14 as will be described below.

The intermediate plate 14 is preferably constructed of metal. However, other materials of sufficient stiffness and toughness could also be used. Ceramics such as zirconia are possible materials. The plate 14 has a flat proximal surface 42 which will be adjacent the surface 34 when the prosthesis is assembled, and a distal surface 44 which will be adjacent a resected surface of the tibia when the prosthesis is implanted in the human body. Between the two surfaces 42, 44 is a curved edge 46 which conforms generally to the edge 24 of the main body 12. When the prosthesis has a cruciate ligament-sparing design, there may also be a notch 48 which corresponds to the notch 26 mentioned in connection with the main body 12. The notch may be omitted for a posterior stabilized knee prosthesis design. In the plate 14 there is a cruciate opening 50 which slides over the cruciate stem 28 and locks as will be more particularly described below. I have also provided at least one, preferably more than one and more preferably four pegs 52 on the proximal surface of the plate 14. These pegs 52 fit into the slots 40 on the body 12 and prevent rotation of the plate 14 with respect to the body 12.

The cruciate hole 50 has a medial extension 54, a lateral extension 56, an anterior extension 58 and a posterior extension 60. The medial and lateral extensions 54, 56 each has an orthogonal lobe, 62, 64 respectively, which lobes will line up with the medial and lateral arms 30, 32 of the stem 28 when the prosthesis 10 is assembled. The medial and lateral extension further comprise offset lobes 66, 68 respectively. The offset lobes 66, 68 form an opening which has a long dimension from the end of the medial offset lobe 66 to the end of the lateral offset lobe 68 which equals or exceeds the greatest dimension of the medial and lateral arms 30, 32. The anterior and posterior extensions 58, 60 similarly have offset anterior and posterior lobes 70, 72 respectively which form an opening having a long dimension from the end of the anterior offset lobe to the end of the posterior offset lobe equal to or greater than the anterior-posterior dimension of the anterior and posterior arms 36, 38 of the stem. Anterior and posterior orthogonal lobes may also be provided at right angles to the anterior and medial orthogonal lobes 62, 64 or the anterior posterior dimension of the cruciate hole 50 may simply be large enough to accommodate the stem 28, as will be more particularly described below. The ends of the extensions 54, 56, 58, 60, adjacent the lobes 62, 64, 70, 72 form tabs 63, 65, 71, 73 which will be captured in the slots 39 when the prosthesis is assembled.

Figure 2:
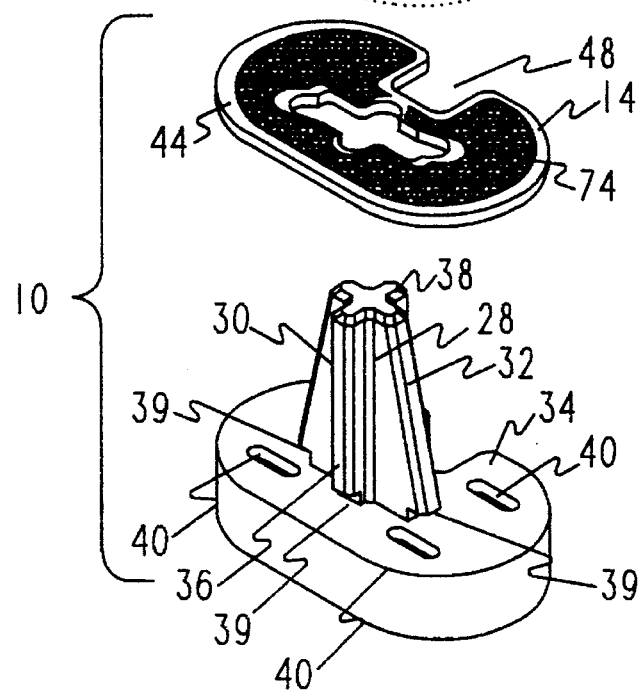
FIG. 2 is an inverted perspective view of the tibial prosthesis of FIG. 1 with the baseplate again illustrated in two position, in solid and phantom lines.

To assemble the prosthesis 10 of my invention, the intermediate plate 14 is presented to the body 12 with the offset slots aligned with the arms of the stem 28 as shown by a phantom intermediate plate 14' in FIG. 1 or FIG. 2. The plate is then advanced along the stem 28 until it comes in contact with the distal surface 34. The plate 14 is then rotated such that the orthogonal slots 62, 64 aligned with the medial and lateral arms 30, 32. In the illustrated embodiment and as shown in FIG. 1, this would mean rotating the baseplate about 5 to 10 degrees clockwise. As the lobes 62, 64 contact the arms 30, 32 the tabs 63, 65, 71, 73 of the plate 14 are captured in the notches 39 at the proximal ends of the arms 30, 32 and 36, 38. Moreover, the pins 52 snap into the slots 40 in the body 12 preventing the disassembly of the plate 14 and the body 12. The prosthesis is now locked together and can be implanted in the body in a known fashion. The stem 28 provides fixation and stability. The distal surface 44 of the plate 14 may be provided with porous coating 74, as is known in the art. It would be expected that adjacent the resected proximal surface of the tibia, bone would grow into the porous coating 74, further securing the tibial prosthesis to the bone.

Those skilled in the art will recognize that my invention can be embodied in other specific forms without departing from the spirit or teaching thereof. The scope of my invention is to be defined by the appended claims and the foregoing description is to be considered illustration and not restrictive.

I claim as my invention:

1. A tibial component of a knee prosthesis comprising a body and a support plate,
   said body having
      a proximal plate adapted to lie near a proximal resected surface on a patient's tibia, said plate having a distal surface and an articulating surface forming a medial condyle compartment and a lateral condyle compartment and
      a central stem integral with said plate adapted to be inserted into a prepared cavity in the medullar canal of the patient, said stem having at least one peripheral slot adjacent and parallel to said distal surface for fastening said support plate to said body, and said support plate having
      a proximal surface adapted to fit against said distal surface of said proximal plate,
      an affixation surface adapted to fit against said proximal resected surface on the patient's tibia,
      a central opening through which the stem fits, and
      at least one peripheral tab extending into said central opening for engaging said slot whereby said support plate is attached to said body.

2. The tibial component according to claim 1 wherein said body is formed entirely from a single piece of biocompatible polymer.

3. The tibial component according to claim 2 wherein said support plate is comprised substantially completely of metal.

4. The tibial component according to claim 1 wherein said at least one slot comprises at least two slots located radially opposite each other across said stem and wherein said at least one tab comprise at least two tabs located radially opposite each other across said central opening.

5. The tibial component according to claim 4 wherein the stem has a cruciate cross-section with four orthogonal extensions, each extension having a slot at a base thereof adjacent said distal surface of said proximal plate, and said central opening has a corresponding cruciate perimeter forming four orthogonal openings, each opening subtending an arc equal to at least twice the arc subtended by an associated extension, and each opening having a tab extending thereinto.

6. The tibial component according to claim 5 wherein said body is formed substantially entirely from a biocompatible polymer.

7. The tibial component according to claim 6 wherein said polymer is ultra high molecular weight polyethylene.

8. The tibial component according to claim 6 wherein said support plate is comprised substantially completely of metal.

9. The tibial component according to claim 8 wherein the support plate has a porous coating on said affixation surface.

10. The tibial component according to claim 1 further comprising means for locking said tab into said slot by inhibiting reverse rotation of said support plate.

11. The tibial component according to claim 10 wherein said at least one slot comprises at least two slots located radially opposite each other across said stem and wherein said at least one tab comprise at least two tabs located radially opposite each other across said central opening.

12. The tibial component according to claim 11 wherein the stem has a cruciate cross-section with four orthogonal extensions, each extension having a slot at a base thereof adjacent said distal surface of said proximal plate, and said central opening has a corresponding cruciate perimeter forming four orthogonal openings, each opening subtending an arc equal to at least twice the arc subtended by an associated extension, and each opening having a tab extending thereinto.

13. The tibial component according to claim 12 wherein said body is formed substantially entirely from a biocompatible polymer.

14. The tibial component according to claim 13 wherein said polymer is ultra high molecular weight polyethylene.

15. The tibial component according to claim 13 wherein said support plate is comprised substantially completely of metal.

16. The tibial component according to claim 15 wherein the support plate has a porous coating on said affixation surface.

* * * * *